(12) United States Patent
Schmitt

(10) Patent No.: US 9,841,318 B1
(45) Date of Patent: Dec. 12, 2017

(54) APPARATUS FOR ACOUSTIC SENSING

(71) Applicant: SONAVATION, INC., Palm Beach Gardens, FL (US)

(72) Inventor: Rainer M. Schmitt, Palm Beach Gardens, FL (US)

(73) Assignee: SONAVATION, INC., Palm Beach Gardens, FL (US)

( * ) Notice: Subject to any disclaimer, the term of this patent is extended or adjusted under 35 U.S.C. 154(b) by 438 days.

(21) Appl. No.: 14/478,671

(22) Filed: Sep. 5, 2014

Related U.S. Application Data

(63) Continuation-in-part of application No. 13/289,391, filed on Nov. 4, 2011, now abandoned, and a continuation-in-part of application No. 13/098,964, filed on May 2, 2011, now abandoned, and a continuation-in-part of application No. 13/277,021, filed on Oct. 19, 2011, now abandoned.

(60) Provisional application No. 61/410,236, filed on Nov. 4, 2010, provisional application No. 61/329,605, filed on Apr. 30, 2010, provisional application No. 61/394,569, filed on Oct. 19, 2010.

(51) Int. Cl.
| | |
|---|---|
| *G01N 29/09* | (2006.01) |
| *G01H 15/00* | (2006.01) |
| *A61B 8/00* | (2006.01) |
| *G01S 7/521* | (2006.01) |
| *G01S 7/52* | (2006.01) |
| *A61B 8/08* | (2006.01) |

(52) U.S. Cl.
CPC ........... *G01H 15/00* (2013.01); *A61B 8/4494* (2013.01); *A61B 8/485* (2013.01); *A61B 8/52* (2013.01); *G01N 29/09* (2013.01); *G01S 7/521* (2013.01); *G01S 7/52036* (2013.01); *G01S 7/52038* (2013.01); *G01S 7/52079* (2013.01)

(58) Field of Classification Search
CPC .......... G01H 15/00; G01N 29/09; A61B 8/52; A61B 8/44; A61B 8/4494; A61B 8/485; G01S 7/52036; G01S 7/52038; G01S 7/52079; G01S 7/52042; G01S 7/521; G06K 9/0002
USPC ..................... 73/589; 600/442, 459; 310/327
See application file for complete search history.

(56) References Cited

U.S. PATENT DOCUMENTS

| | | | |
|---|---|---|---|
| 6,159,149 A * | 12/2000 | Erikson | A61B 8/4483 600/437 |
| 2002/0135272 A1* | 9/2002 | Toda | B06B 1/0292 310/334 |
| 2009/0108710 A1* | 4/2009 | Brown | B06B 1/0622 310/367 |
| 2009/0279747 A1* | 11/2009 | Schmitt | G06K 9/0002 382/124 |

(Continued)

FOREIGN PATENT DOCUMENTS

JP          2012235925 A     *  12/2012

*Primary Examiner* — Laura Martin
*Assistant Examiner* — Rose M Miller
(74) *Attorney, Agent, or Firm* — Lukacher Law Group; R.S. Rosenholm

(57) ABSTRACT

The invention provides an improved acoustic energy generating apparatus that includes an improved backing structure. The improved backing structure employs protrusions that are not located in a uniform pattern along a forward side surface of the backing structure, to realize improved redirection of acoustic energy towards a forward direction relative to the acoustic energy generating apparatus.

15 Claims, 4 Drawing Sheets

(56) References Cited

U.S. PATENT DOCUMENTS

2009/0279748 A1* 11/2009 Schmitt ............... G06K 9/0002
382/124
2009/0279751 A1* 11/2009 Schmitt ............... G06K 9/0002
382/125

* cited by examiner

APPARATUS FOR ACOUSTIC SENSING

CROSS REFERENCE TO RELATED APPLICATIONS

This document is a U.S. non-provisional utility patent application of the continuation-in-part application type, and that is a continuation-in-part of, and claims priority and benefit to, U.S. non-provisional patent application Ser. No. 13/289,391, which was filed on Nov. 4, 2011, and entitled "Touch Fingerprint Sensor Using 1-3 Piezo Composites and Acoustic Impediography Principle", and which claims priority and benefit to U.S. provisional utility patent application Ser. No. 61/410,236 which was filed on Nov. 4, 2010. Priority is claimed to all of the aforementioned patent applications, which are each incorporated herein by reference in their entirety.

This document is a continuation-in-part of, and further claims priority and benefit to, U.S. non-provisional utility patent application Ser. No. 13/098,964, which was filed on May 2, 2011, and entitled "Method for Making Integrated Circuit Device Using Copper Metallization on 1-3 PZT Composite", and which claims priority and benefit to U.S. provisional utility patent application Ser. No. 61/329,605 which was filed on Apr. 30, 2010. Priority is claimed to all of the aforementioned patent applications, which are each incorporated herein by reference in their entirety.

This document is a continuation-in-part of, and further claims priority and benefit to, U.S. non-provisional utility patent application Ser. No. 13/277,021, which was filed on Oct. 19, 2011, and entitled "Electrical System, Method, and Apparatus of Fingerprint Sensor Using Acoustic Impediography", and which claims priority and benefit to U.S. provisional utility patent application Ser. No. 61/394,569 which was filed on Oct. 19, 2010. Priority is claimed to all of the aforementioned patent applications, which are each incorporated herein by reference in their entirety.

REFERENCE TO APPLICATIONS INCLUDING RELATED SUBJECT MATTER

This document also includes subject matter relating to that of U.S. Patent Publication No: 2010/0237992, and to that of U.S. Patent Publication No: 2009/0279747, and to that of U.S. Patent Publication No: 20100239133, which issued as U.S. Pat. No. 8,508,103. All of these (3) aforementioned patent publications, are each incorporated herein by reference in their entirety.

BACKGROUND OF THE INVENTION

Acoustic impedance sensors transmit acoustic energy and can be employed to measure human characteristics, including biometric characteristics.

The discussion above is merely provided for general background information and is not intended to be used as an aid in determining the scope of the claimed subject matter.

BRIEF DESCRIPTION OF THE INVENTION

The invention provides embodiments of a design of an acoustic impedance sensor including embodiments of a backing structure.

This brief description of the invention is intended only to provide a brief overview of subject matter disclosed herein according to one or more illustrative embodiments, and does not serve as a guide to interpreting the claims or to define or limit the scope of the invention, which is defined only by the appended claims.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention can encompass other equally effective embodiments. The drawings are not necessarily to scale. The emphasis of the drawings is generally being placed upon illustrating the features of certain embodiments of the invention.

In the drawings, like numerals are used to indicate like parts throughout the various views. Differences between like parts may cause those parts to be indicated with different numerals. Unlike parts are indicated with different numerals. Thus, for further understanding of the invention, reference can be made to the following detailed description, read in connection with the drawings in which.

DETAILED DESCRIPTION OF THE INVENTION

Figure 1:
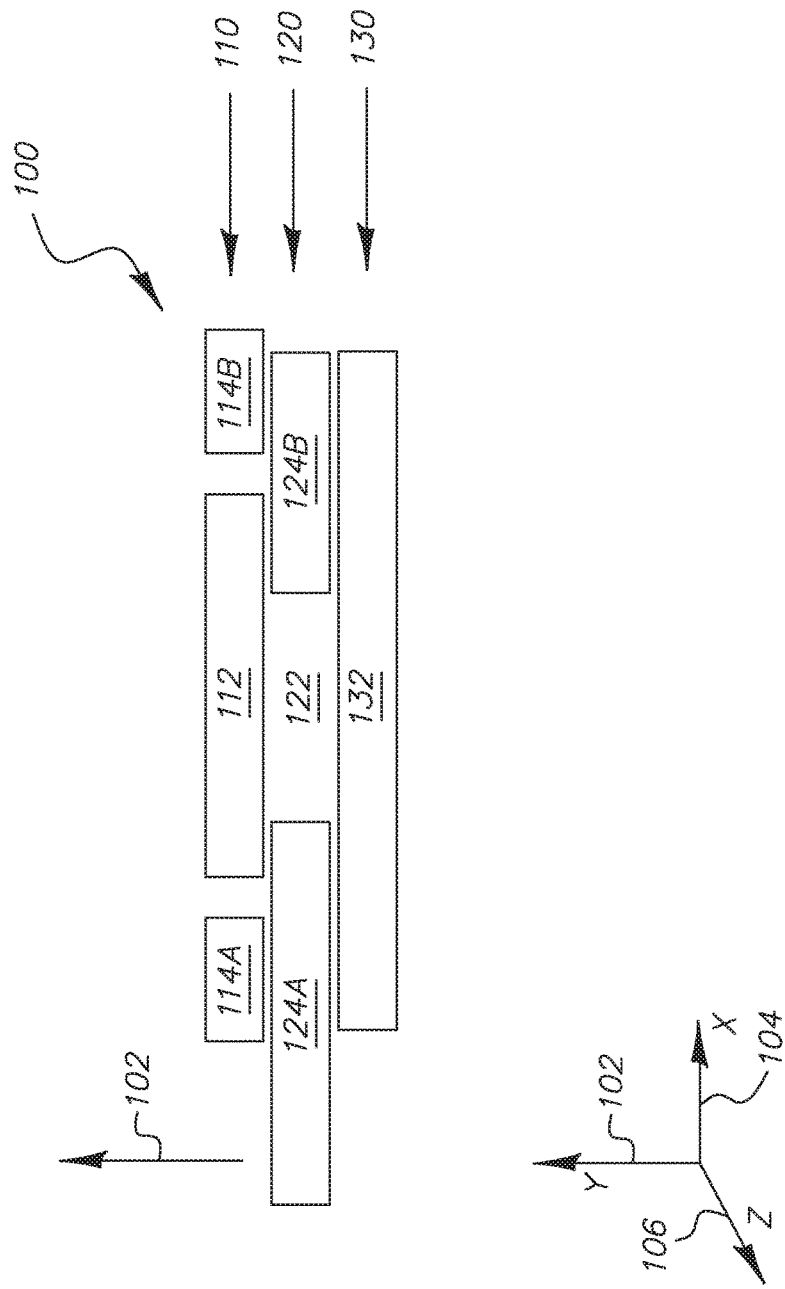
FIG. 1 illustrates a cross-sectional view of a first embodiment of an acoustic impedance sensing apparatus.

FIG. 1 illustrates a cross-sectional view an acoustic impedance sensing apparatus 100. As shown, the apparatus 100 includes a first layer 110, a second layer 120 and a third layer 130 of components. A first layer of components 110 includes an acoustic impedance sensor 112, also referred to herein as a sensor 112. The sensor 112 is disposed in between other components 114a-114b which function as a bezel, and are also referred to as bezel components 114a-114b. A second layer of components 120 includes support structures 124a-124b and an air gap 122. The air gap 122 is located adjacent and below a lower side of the sensor 112. A third layer of components 130, also referred to herein as a backing layer 130, is disposed adjacent to a lower side of the air gap 122.

In some embodiments, the sensor 112 is employed as a fingerprint touch sensor. In this embodiment, one or more fingers are disposed proximate to an upper surface of the sensor 112. While in operation, the acoustic energy is directed from the sensor 110 towards soft tissue of the one or more human fingers disposed in proximity to the upper surface of the sensor 110.

Ideally, the acoustic impedance sensor 110 directs all acoustic energy in a forward direction that is upward 102 and away from the acoustic impedance sensing apparatus 100, as shown here. However, in practice, acoustic energy can be drawn away from the sensor 112 in many directions. In circumstances without an air gap 122 and without a backing layer 130 that is adjacent to and bounding the air gap 122, a substantial portion of acoustic energy would likely be drawn away from the sensor 112, in directions other than the forward direction 102, where the forward direction is shown as being an upward direction along the Y axis 102 in FIGS. 1-2.

For example, in accordance with the Redwood Transient Model, with the apparatus 100 having the air gap 122 and backing layer 130 as shown in FIG. 1, the output amplitude of the acoustic energy that is being transmitted by the sensor 112, in the upward (forward) direction 102, is increased by 30%, as compared to an amplitude of acoustic energy transmitted in the upward (forward) direction without the air gap 122 and without the backing layer 130 including a backing layer component 132 of a particular structure and design. The backing layer component 132 is also referred to herein as a backing layer structure 132, as a backing component structure 132 or simply as a backing structure 132.

The backing layer structure 132 can be designed to provide mechanical support for the components of the other layers 110 and 120. In this role, the backing layer structure 132 is also referred to herein as a stiffener. For the backing layer structure 132 to be effective towards increasing an amount of upward transmission of acoustic energy, the backing layer structure 132, as a rearward medium relative to the upper (forward) side of the sensor 112, should have a lower, and preferably a much lower, acoustic impedance than that of any forward medium relative to the upper (forward) surface of the sensor 112. When the sensor 112 is designed as a fingerprint touch sensor, the forward medium would be the soft tissue of fingers disposed above and proximate to the upper surface of the sensor 112 (See FIG. 4).

In some embodiments, the backing layer structure 132 is made from material having an acoustic impedance of about as low as 0.5 MRayl. This MRayl value is much lower than that of the pillar material and is lower than the acoustic impedance of any finger tissue that is disposed above the upper surface of the sensor 112. Materials, such as those made from air gel and/or made from composite material including hollow glass spheres, can be employed to construct the backing layer structure 132 having such a low acoustic impedance of about 0.5 MRayl.

Although air has a low acoustic impedance value of just 1.2 KRayls, the air pocket 122 can collect moisture over time. Such moisture can interfere with the operation of the sensor 112.

Figure 2:
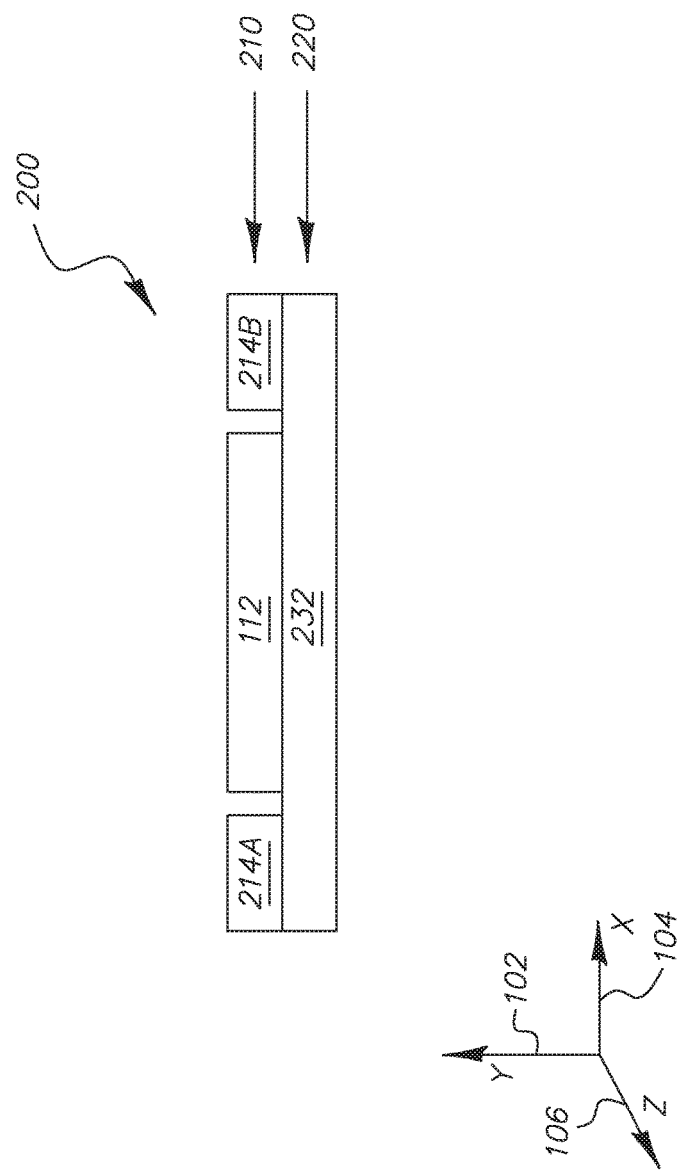
FIG. 2 illustrates a cross-sectional view of a second embodiment of an acoustic impedance sensing apparatus.

FIG. 2 illustrates a cross-sectional view of a second embodiment of an acoustic impedance sensing apparatus. As shown, the apparatus 200 includes a first layer 210, a second layer 220 of components. Like FIG. 1, the first layer of components 110 includes an acoustic impedance sensor 112 and bezel components 214a-214b. Unlike the FIG. 1, this embodiment includes two and not three layers, and lacks a second layer like that of FIG. 1, and as a result, does not employ an air gap. Instead, the second layer 220 is made as one solid backing component 232. This embodiment is designed to address the moisture problems caused by employing an air gap, and is designed for providing structural support for other components in the acoustic sensing apparatus, if necessary.

In some embodiments, the second layer is molded and is also referred to as a molded backer 232 or molded base 232. This backing component 232 is designed to make limited physical contact with a lower (back and rearward) side of the sensor 12.

Figure 4:
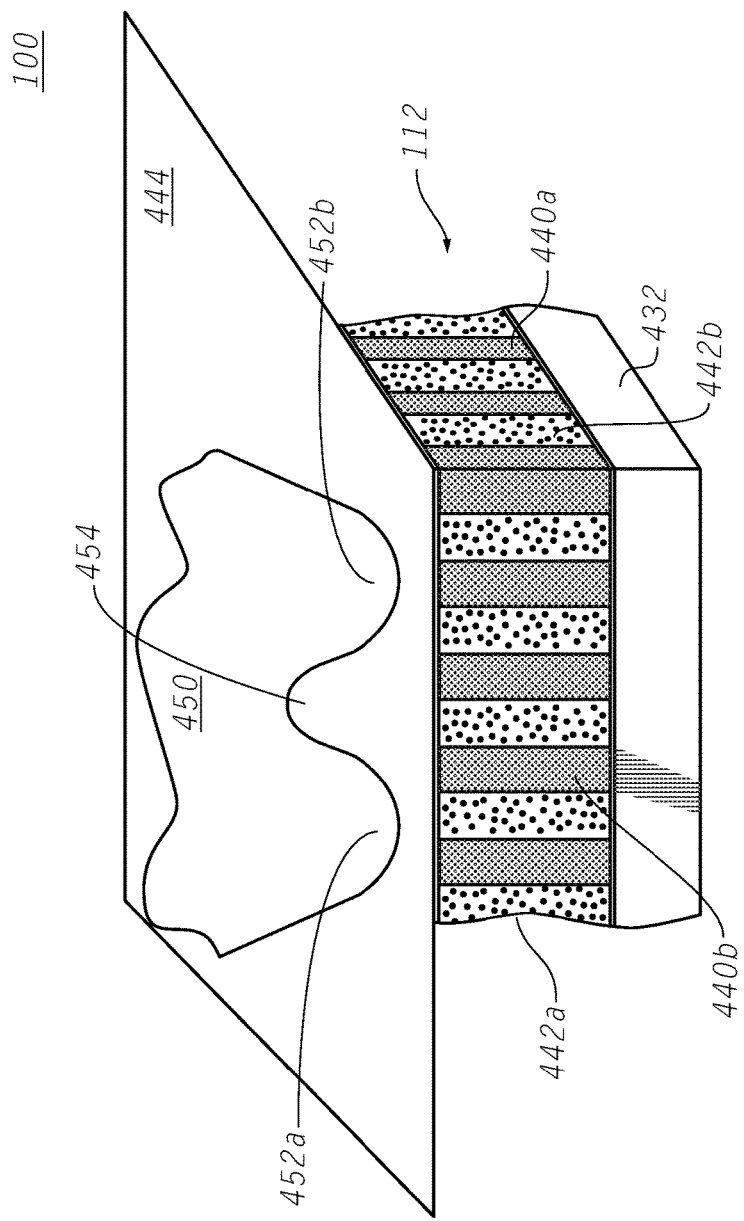
FIG. 4 illustrates a side perspective view of an embodiment of a sensor, being an acoustic impedance sensing apparatus that is designed to sense surface characteristics of a finger that is direct physical contact with the sensor.

Like the third layer 130 of FIG. 1, the backing layer component 232 is made from a material having lower acoustic impedance, than material located forward (above) the top surface of the sensor 112, also referred to herein as (forward material or forward medium), such as finger tissue, that is disposed above the upper and forward surface of the sensor 112 during its operation (See FIG. 4).

Unlike the third layer 130 of FIG. 1, the backing layer 232 includes a pattern of distributed protrusions, which are also referred to as "bumps", along its upper and forward surface. In accordance with the invention, this pattern of protrusions is preferably non-uniformly distributed. This pattern of protrusions is designed to reduce a loss (transfer) of acoustic energy from the sensor 112 in a rearward direction towards the backing layer component 232 of the backing layer 220, by in part, reducing an amount of physically contacting surface area, between the lower (back and rearward) side of the sensor 112 and the upper side of the backing layer component 232. The rearward direction being in an opposite direction relative to the forward direction.

Note that experimental results show that a non-uniform distribution of protrusions (bumps) reduces an amount of transfer of acoustic energy from the sensor 112 to the backing layer component 232, relative to an amount of acoustic energy transfer that would occur via a uniform protrusion (bump) distribution pattern including a same number and size of protrusions (bumps).

Figure 3:
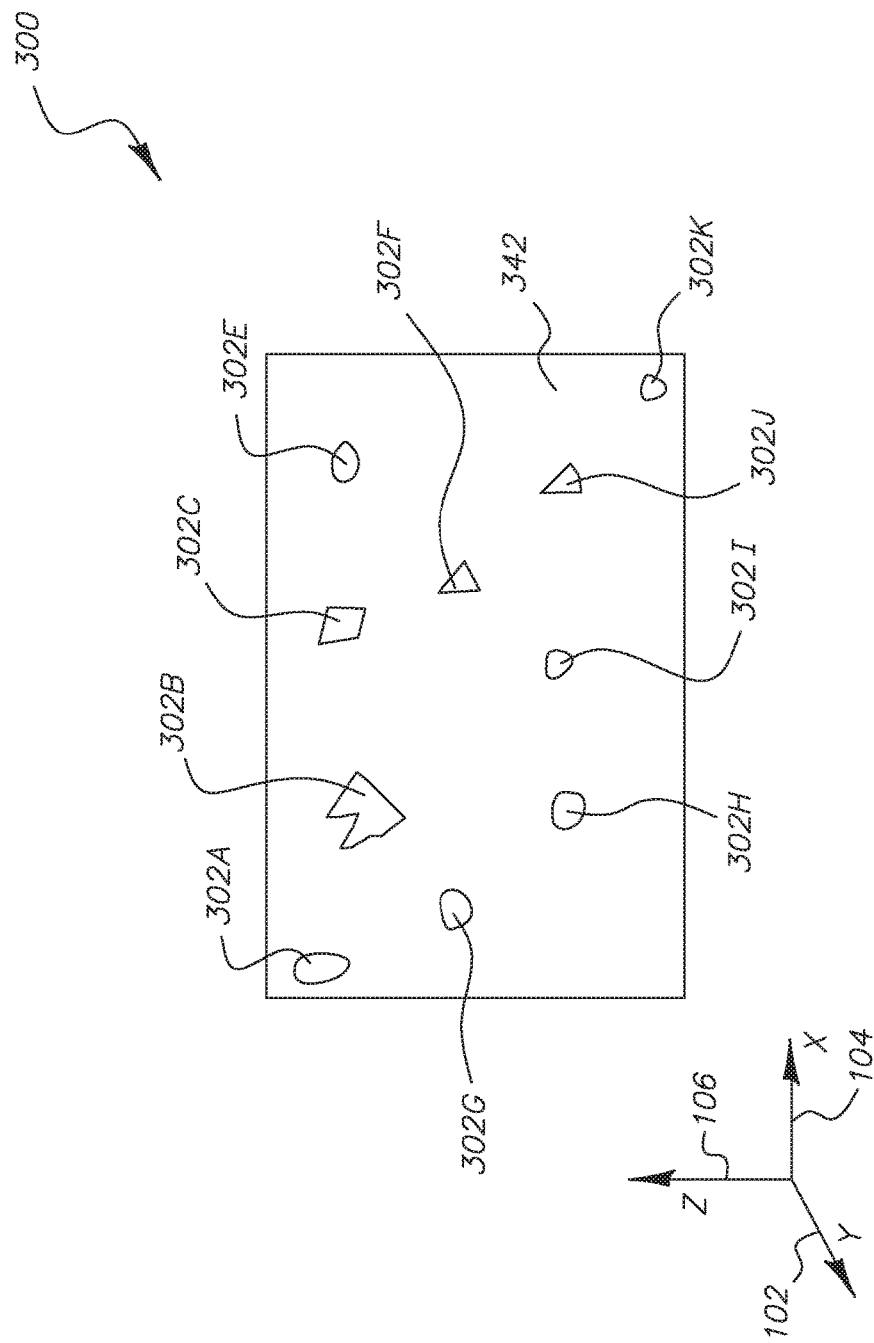
FIG. 3 illustrates a cross-section view parallel to the X and Z axes, of the upper surface of the backing layer structure.

FIG. 3 illustrates a cross-sectional view of the upper surface 342 of the backing layer 232. As shown, this view is parallel to the X 104 and Z 106 axes. During manufacturing of the acoustic impedance sensor 112, the upper side of the backing layer component 232 makes physical contact with, and could be pressed against the lower side of the sensor 112. As a result, various shaped contact areas 302a-302k are created by protrusions (bumps) from the upper side of the backing layer component 232 touching the lower and rearward side of the sensor 112. As shown, these contact areas 302a-302k are not restricted to having a particular two dimensional shape. Also note that the shape and size of both the upper surface 342 and the contact areas 302a-302k are to describe a concept, and embodiments of the invention are not limited to shape or scale of the upper surface 342, nor to the shape, scale or number of contact areas 302a-302k.

In some embodiments, the protrusions (bumps) are manufactured to have a consistent dimension and shape, and contact areas associated with these protrusions are more uniform with respect to their shape and size. In other embodiments, the protrusions (bumps) are not manufactured to have a consistent dimension and shape, and contact areas associated with these protrusions are less uniform with respect to their shape and size.

For example, these protrusions can have a shape and size distribution like that of a mountain range, for example, yielding a rough surface when touched. During manufacturing of the sensor 112, the tops of the protrusions, which are shaped like mountains that are disposed along the upper (forward) surface of the backing structure, are bent and/or broken off when pressed against the lower side of the sensor 112, to form contact area patterns like that shown in FIG. 3.

In accordance with the invention, the spatial distribution of these contact areas is preferably non-uniform. Also and preferably, each contact area is limited in size. In some embodiments, each contact area is less than the cross-sectional area of a pillar within the sensor 112.

Within the sensor 112, a first pillar is surrounded by spacing between the first pillar and other surrounding and adjacent pillars. For example, if a pillar has a 150 um height dimension (parallel to the Y axis 102), and a square cross-section formed by a first width dimension of 50 um (parallel to the X axis 104) and formed by a second width dimension ((parallel to the Z axis 106) of 50 um, then the cross-sectional area of the first pillar, that is parallel to the X-Z plane, is 50 um×50 um=2500 square um.

A longest line that can be drawn within this cross-sectional area would be a diagonal line (hypotenuse) drawn between opposite corners of this square cross-section. This longest line would have a length equaling the square root of ((50 um squared)+(50 um squared)), which would be equal to approximately 70.71 um. The length of this longest line is also referred to herein as the longest span or span within the cross-sectional area of the pillar.

A unit cell is the cross-sectional area of the pillar along the X-Z plane, as described above, plus one half of the surrounding gap (pitch) between pillars. For example, if the gap (pitch) between pillars is uniformly 72 um, then the cross-sectional area of the unit cell along the X-Z plane is equal to (50 um+72/2 um)×(50 um+72/2 um)=7396 square um. The longest span within that unit-cell cross sectional area is equal to the square root of ((70.71 um squared)+(70.71 um squared)), which equals a length of about 100 um.

Note that each contact area, regardless of its shape and size, also has a longest span, which is a longest line that can be drawn within the cross-sectional area of the contact area, parallel to the X-Z plane. In some embodiments, the span of most or of all contact areas, is less than or equal to that of the span of a pillar unit cell. In other embodiments, such spans are less than or equal to that of a span of a pillar cross-section. Limiting contact areas within such short spans reduces loss of acoustic energy in the rearward direction.

Experimental results indicate that, maximizing the difference between the acoustic impedance values of the material of the pillars and of the material of the backing structure 232, increases reflection of acoustic energy by the backing structure, from the rearward to the forward direction. These results also indicate that minimizing individual and/or the total contact area between the backing structure 232 and the sensor 112 reduces loss of acoustic energy in the rearward direction from the sensor 112. These experimental results also indicate that non-uniform distribution of individual contact areas between the sensor 112 and the backing structure 232 reduces the loss of acoustic energy in the rearward direction.

In some embodiments, pillars are made from a piezoelectric composite material which typically has an acoustic impedance value of 10 MRayl or higher. Selecting backing structure materials with a much lower MRayl value than 10 MRayl, is a way of creating an acoustic impedance difference between the sensor 112 and the backing structure 232 in order to cause reflection of acoustic energy to the forward direction and/or to reduce loss of acoustic energy in the rearward direction.

In accordance with the invention, materials with a higher MRayl value than that of the pillars can be selected to manufacture a backing structure 232, however such materials, for example, tungsten having a high 100 MRayl value, yields an acoustic energy reflection co-efficient equal to about 74%, as opposed to 0.5 MRayl or less materials which are each instead expected to yield a higher reflection co-efficient than that of tungsten.

Hence, the reflection effect of the difference with respect to the MRayl value of the pillars and of the backing structure 232, is expected to be generally less with higher than available 10 MRayl value backing structure material, than the reflection effect caused by that of available low MRayl value backing structure materials, especially those materials at or below 0.5 MRayl. However, there is room for improvement, where materials having even lower, for example 0.1 MRayl, would measurably improve the reflection effect with respect to the acoustic impedance difference between the pillars of the sensor 112 and the backing structure 232.

FIG. 4 illustrates a side perspective view of an embodiment of a sensor 112, being an acoustic impedance sensing apparatus that is designed to sense surface characteristics of finger tissue 450 that is direct physical contact with an upper surface of the sensor 112. As shown, the sensor 112 includes a set of pillars 440, which includes two individual pillars 440a-440b as shown. These pillars are also referred to as elements, vibrating elements or pixels. In this particular embodiment, the pillars are made from a piezo ceramic material, and are arranged into a two dimensional array. Each of the pillars 440 is designed to oscillate over time in response to an electrical voltage that also oscillates over time, and that is applied across the length (longest dimension) of each pillar 440. The pillars abut interstitial filler material 442 that is also disposed inside of the two dimensional array of pillars 440.

The finger tissue 450 is shown to be expanded in size to reveal a fingerprint valley 454 that is surrounded by neighboring fingerprint ridges 452a-452b. The finger tissue 450 is disposed onto an upper protection layer 444 of the sensor 112 which forms an upper surface of the sensor 112 and which is disposed above the two dimensional array of pillars 440. The oscillation characteristics of each pillar of the array of pillars 440 is measured to detect a presence of a fingerprint valley 454 or fingerprint ridge 452a-452b of the finger tissue 450 that could potentially be located directly above each oscillating pillar 440.

Note that a first conductor grid, referred to as the upper conductor grid, resides within a thin volume of (thin layer) of space that is disposed above and abuts an upper side of the array of pillars 440. A second conductor grid, referred to as a lower conductor grid, also resides within a thin volume (thin layer) of space that is disposed below and abuts a lower side of the array of pillars 440. Both of the upper and lower conductor grid layers reside within the sensor 112 and are designed to apply a voltage across each of the pillars of the array of pillars 440 of the sensor 112.

As shown, an embodiment of a backing component 432, also referred to herein as a backing structure 432, as described above, is disposed below and abuts the lower side of the sensor 112. Hence, the backing component 432 is disposed below and preferably abuts the lower conductor grid, which abuts and is located below the two dimensional array of pillars 440. Both the lower conductor grid and the array of pillars 440, residing within the sensor 112.

This written description uses examples to disclose the invention and also to enable a person skilled in the art to practice the invention, including making and using any devices or systems and performing any incorporated methods. The patentable scope of the invention is defined by the claims, and may include other examples that occur to those skilled in the art.

What is claimed is:

1. An acoustic impedance sensing apparatus, comprising:
   a set of oscillating pillars that transmit acoustic energy within an acoustic impedance sensor; and where said pillars are designed to direct said acoustic energy in at least a forward direction; and
   a backing structure that is made from a material having an acoustic impedance characteristic that is less than that of material from which said pillars are made from, said backing structure including protrusions along a forward surface of said backing structure, said protrusions abutting a rearward surface of said acoustic impedance sensor; said rearward surface of said acoustic impedance sensor being opposite of a forward surface of said acoustic impedance sensor, and where said protrusions are located to make physical contact with said rearward surface of said acoustic impedance sensor and where said protrusions are not located in a uniform pattern along said forward surface of said backing structure.

2. The apparatus of claim 1 wherein said protrusions are located in a random pattern.

3. The apparatus of claim 1 wherein a majority of said protrusions have a contact area abutting said rearward surface of said acoustic impedance sensor of an amount that is less than or equal to a cross-sectional area of a unit cell of at least one of said pillars.

4. The apparatus of claim 1 wherein a majority of said protrusions have a contact area of an amount that is less than a cross-sectional area of a unit cell of at least one of said pillars.

5. The method of claim 1 wherein a majority of said protrusions have a contact area having a span that is less than or equal to a span a of a unit cell of at least one of said pillars.

6. A method of making an acoustic impedance sensor, comprising the steps of:
providing an acoustic impedance sensor, said acoustic impedance sensor including oscillating pillars that generate acoustic energy; said acoustic impedance sensor designed to direct said acoustic energy in a forward direction; and
providing a backing structure that is made from a material having an acoustic impedance characteristic that is less than that of said pillars, said backing structure including protrusions along a forward surface of said backing structure, said protrusions abutting a rearward surface of said acoustic impedance sensor; said rearward surface being opposite of said a forward surface of said acoustic impedance sensor, and where said protrusions are located to make physical contact with said rearward surface of said acoustic impedance sensor and where said protrusions are not located in a uniform pattern along said forward surface of said backing structure.

7. The method of claim 6 wherein said protrusions are located in a random pattern.

8. The method of claim 6 wherein a majority of said protrusions have a contact area abutting said rearward surface of said acoustic impedance sensor of an amount that is less than or equal to a cross-sectional area of a unit cell of at least one of said pillars.

9. The method of claim 6 wherein a majority of said protrusions have a contact area of an amount that is less than a cross-sectional area of a unit cell of at least one of said pillars.

10. The method of claim 6 wherein a majority of said protrusions have a contact area having a span that is less than or equal to a width of a unit cell of at least one of said pillars.

11. An acoustic energy transmitting apparatus, comprising:
a set of oscillating pillars that generate acoustic energy within an acoustic energy generator; and that where said pillars are designed to direct said acoustic energy in a forward direction: and
a backing structure that is made from a material having an acoustic impedance characteristic that is less than that of material from which said pillars are made from, said backing structure including protrusions along a forward surface of said backing structure, said protrusions abutting a rearward surface of said acoustic energy generator; said rearward surface of said acoustic energy generator being opposite of said a forward surface of said acoustic energy generator, and where said protrusions are located to make physical contact with said acoustic energy generator and where said protrusions are not located in a uniform pattern along said forward surface of said backing structure.

12. The apparatus of claim 11 wherein said protrusions are located in a random pattern.

13. The apparatus of claim 11 wherein a majority of said protrusions have a contact area abutting said rearward surface of said acoustic energy generator of an amount that is less than or equal to a cross-sectional area of a unit cell of at least one of said pillars.

14. The apparatus of claim 11 wherein a majority of said protrusions have a contact area of an amount that is less than a cross-sectional area of a unit cell of at least one of said pillars.

15. The method of claim 11 wherein a majority of said protrusions have a contact area having a span that is less than or equal to a width a of a unit cell of at least one of said pillars.

* * * * *